US009192706B2

(12) United States Patent
Bulent et al.

(10) Patent No.: US 9,192,706 B2
(45) Date of Patent: Nov. 24, 2015

(54) TRANS ARTERIAL PERMANENT HEART ASSIST DEVICE WITH DOUBLE STATORS

(71) Applicants: Oran Bulent, Konya (TR); Oran Omer Faruk, Konya (TR); Avci Elif Oran, Konya (TR)

(72) Inventors: Oran Bulent, Konya (TR); Oran Omer Faruk, Konya (TR); Avci Elif Oran, Konya (TR)

( * ) Notice: Subject to any disclaimer, the term of this patent is extended or adjusted under 35 U.S.C. 154(b) by 0 days.

(21) Appl. No.: 14/422,003

(22) PCT Filed: Aug. 19, 2013

(86) PCT No.: PCT/TR2013/000274
§ 371 (c)(1),
(2) Date: Feb. 17, 2015

(87) PCT Pub. No.: WO2014/035354
PCT Pub. Date: Mar. 6, 2014

(65) Prior Publication Data
US 2015/0231318 A1    Aug. 20, 2015

(30) Foreign Application Priority Data

Aug. 29, 2012 (TR) .............................. a 2012 09878

(51) Int. Cl.
*A61N 1/362* (2006.01)
*A61M 1/12* (2006.01)
*A61M 1/10* (2006.01)

(52) U.S. Cl.
CPC ............ *A61M 1/122* (2014.02); *A61M 1/1036* (2014.02); *A61M 2205/0238* (2013.01); *A61M 2210/12* (2013.01); *A61M 2230/04* (2013.01)

(58) Field of Classification Search
CPC ........... A61B 19/00; A61M 1/10; F04B 17/00
USPC ..................... 600/16; 623/3; 417/356, 423.12
See application file for complete search history.

(56) References Cited

U.S. PATENT DOCUMENTS

| | | | |
|---|---|---|---|
| 4,944,748 A * | 7/1990 | Bramm et al. ............... | 623/3.14 |
| 5,211,546 A | 5/1993 | Isaacson | |
| 5,290,227 A | 3/1994 | Pasque | |
| 5,957,672 A | 9/1999 | Aber | |
| 2010/0076247 A1 | 3/2010 | Zilbershlag et al. | |
| 2013/0041203 A1 * | 2/2013 | Heilman et al. ................ | 600/16 |

FOREIGN PATENT DOCUMENTS

EP          0060569 A1    9/1982

* cited by examiner

*Primary Examiner* — Christopher D Koharski
*Assistant Examiner* — Roland Dinga
(74) *Attorney, Agent, or Firm* — Gokalp Bayramoglu

(57) ABSTRACT

The invention is a new generation permanent heart assist device developed to be installed into great arteries such as trans-aortic and trans-pulmonary artery to maintain blood circulation of the patients with end-stage heart failure. This device is a sort of brushless, synchronous, servo, electric motor which uses direct driver technology. It consumes little energy and provides high blood flow. The specially designed hollow rotor without a pivot pin provides enough blood flow to the patient by pushing the blood forward with the helical winglets inside it. The risk of thromboembolic events on the foreign surface that contacts with blood is less than in the counterparts of this device. Finally, the invention; is a curved permanent heart assist device that is applied on the aortas, reinforced twice with double stators and designed in smaller size so as not to compress surrounding tissues and organs.

16 Claims, 8 Drawing Sheets

TRANS ARTERIAL PERMANENT HEART ASSIST DEVICE WITH DOUBLE STATORS

TECHNICAL FIELD

Figure 1:
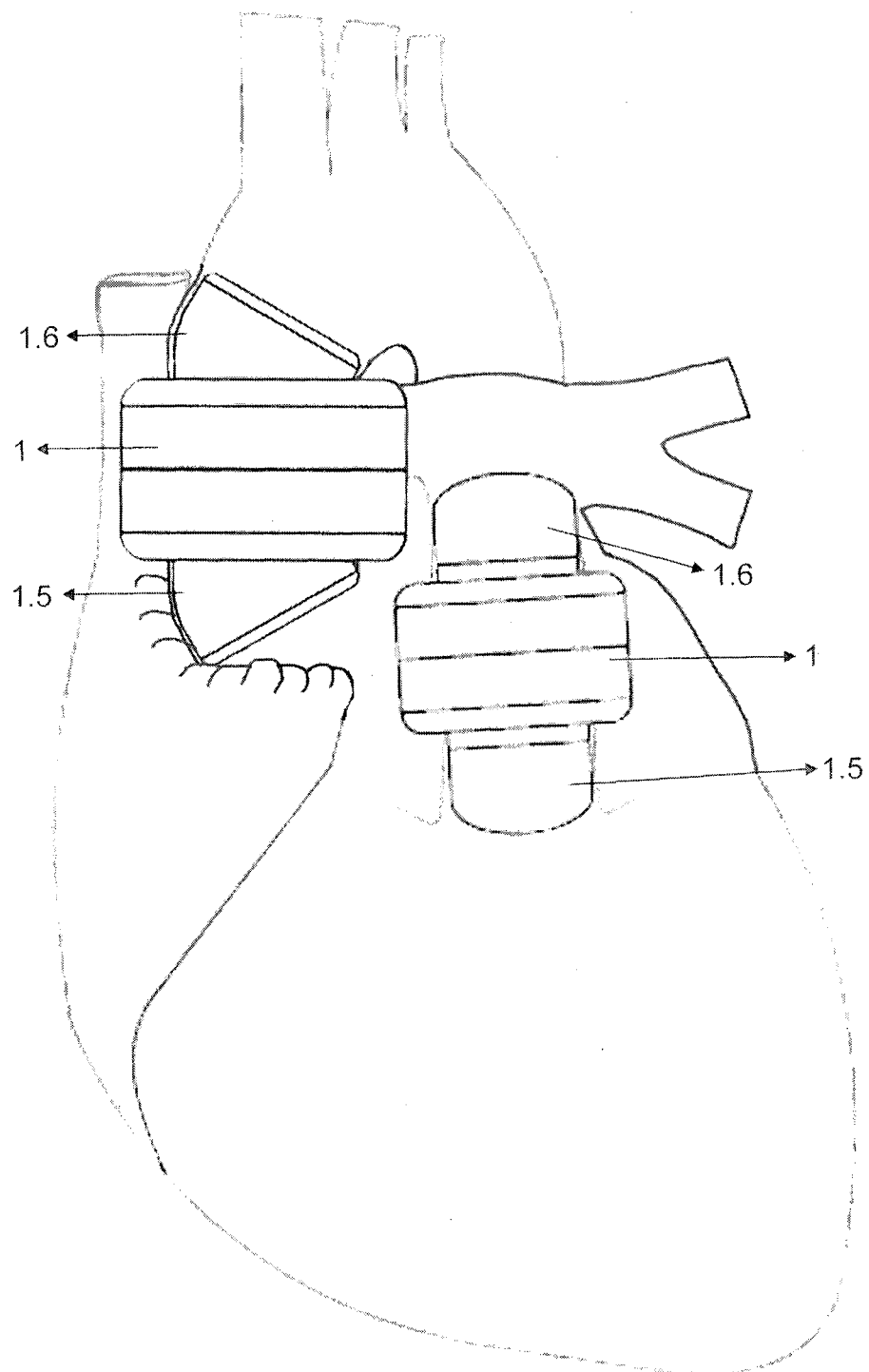

The invention is about a new generation permanent heart assist device developed to be installed into the large arteries such as trans-aortic and trans-pulmonary artery to maintain blood circulation of the patients with end-stage heart failure. The specially designed brushless electric motor used in the device has two separate stators. The rotor revolves on the rollers which contain balls and bearing house made of non-abrasive materials like ceramic.

The fixed magnets outside the rotor are installed facing both stators. There are integrated helical fan blade inside the rotor without a pin, and they provide enough blood flow for the patient by pushing the blood from back to forward when rotor runs. Since both the aorta and pulmonary artery curve after the heart output, the axis of the assist device is designed as curved ergonomically. Briefly, the invention in which direct drive technology was used is a new generation permanent trans aortic heart assist device.

BACKGROUND

Heart assist devices are vital instruments for patients who have contracting hearth muscle problems and who have not responded positively for drug treatments.

The technical problems we have encountered and mentioned in the application for a national patent numbered TR2012/00951 which we presented as a result of our technical studies in this field, and in the application for a international patent numbered PCT/TR 2012/00055 in the framework of the Patent Cooperation Agreement are;

First; the natural magnets and electromagnets, used for magnetic field in order to run the rotor contactless, are significant metal load for the body.

Second; the problems caused by the design of the motor to be faced in the fixation and running of the device without compressing the other blood vessels and organs in the surrounding area have been predicted.

Third; it is vital to regulate the blood flow into the motor, and to prevent turbulence that may occur during the output so as not to affect the shaped elements of the blood.

Fourth; both the aorta and pulmonary artery are curved as an anatomic property, and blood flows in these curved arteries. The present heart assist devices are not sufficient for either to maintain this natural blood flow or help the heart surgeon to install the device.

Fifth; it is essential to ward off the heat increase that may occur as the motor runs from the heart in order to provide healthy results.

BRIEF SUMMARY OF THE INVENTION

It is a permanent trans aortic heart assist device that helps blood circulation in the patients with severe heart failure, and can be inserted into one or two great arteries, i.e. ascending aorta or main pulmonary artery. The rotor, which rotates on the rollers made of ceramic-like materials that are not eroded away by friction, provide enough blood flow by pushing the blood forward with its helical fan blade.

It is a new generation permanent heart assist device which starts during the systole period and stops during the diastole period in turn running synchronously with the signals of electrocardiography (ECG), and contains a synchronous brushless servo electric motor with direct drive technology. Employing ceramic rollers instead of magnetic bearings will enable to rim the device for a long time without any problems requiring no maintenance, and also there will be no serious metal load onto the body.

Moreover, there are specially designed fan blade in the inlet of the device to smooth the blood flow and there are specially designed fan blade in the outlet of the device to adjust the turbulence that may occur in the blood flow. Thanks to the curved parts in the inlet and outlet of the device and with very good heat conductivity, and the fan blade smoothing blood flow and preventing turbulence, it will be possible to move away the heat, which occurs in the motor when it runs, from the heart via blood. Besides, all the surfaces of the device contacting the body will be covered with biocompatible insulating material in order not to let the heat produced when the motor runs hurt the adjacent tissues.

Since it has two stators, it not only enhances its performance but prevents pressure on the surrounding tissues as it has a smaller external diameter. Furthermore, the fact that it has a stand-by stator in case of a trouble in one of the stators is a plus value. When it is compared with its counterparts, this new heart assist device system is presented as a different concept with high performance. The foreign surface contacting blood is relatively limited when it is compared with its counterpart assist devices. Our invention is a new generation heart assist device with an extraordinary design which is installed into the aortas, has no considerable pressure on the surrounding tissues or organs, has a smaller volume and consequently consumes low energy and results in a longer battery life when compared with its counterparts.

LIST OF FIGURES

FIG. 1 The Outlook of the Permanent Heart Assist Device with Double Stators Installed as Trans Pulmonary Artery and Trans Aortic.

Figure 2:
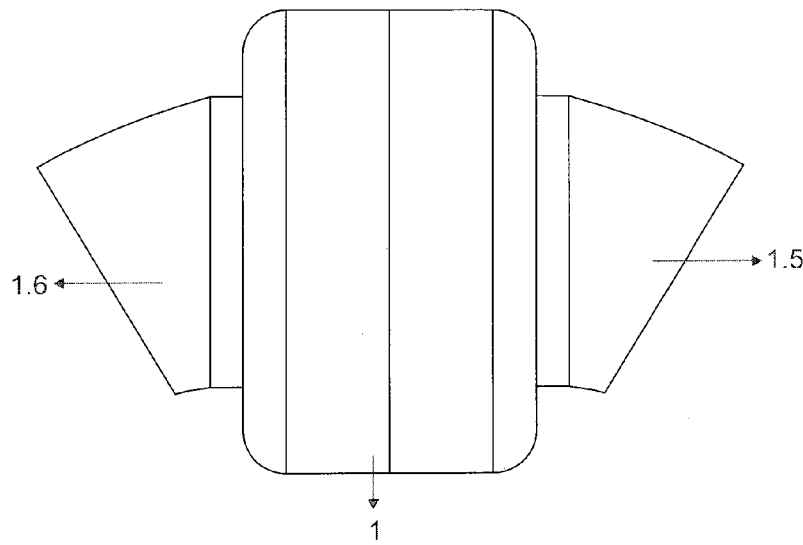

FIG. 2 The General View of the Installed Permanent Heart Assist Device with Double Stators.

Figure 3:
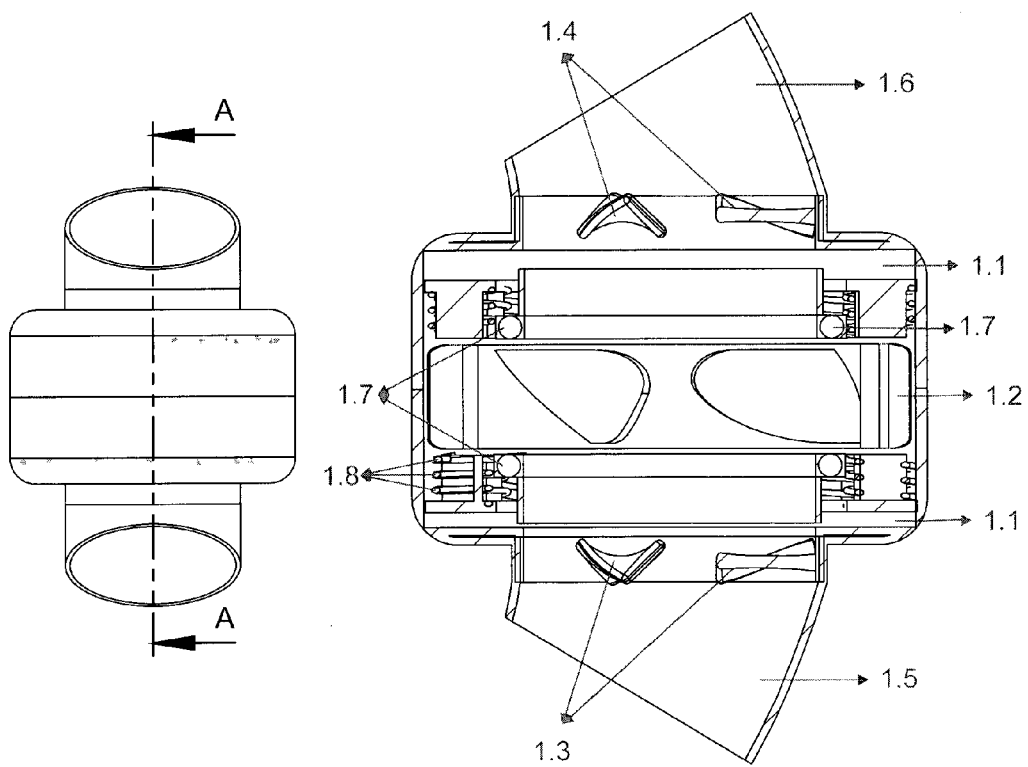

FIG. 3 The Vertical Section View of the Permanent Heart Assist Device with Double Stators.

Figure 4:
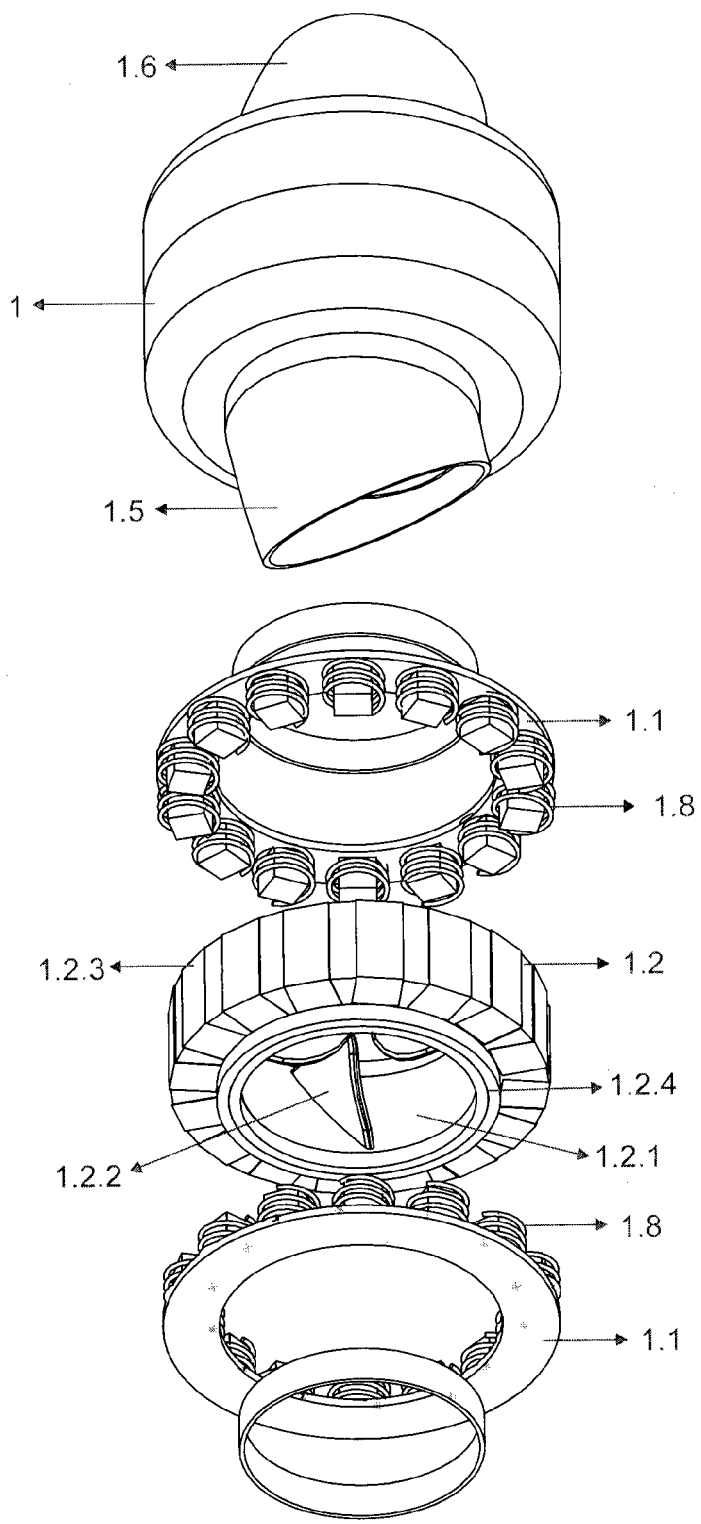

FIG. 4 The Exploded View of the Permanent Heart Assist Device with Double Stators.

Figure 5:
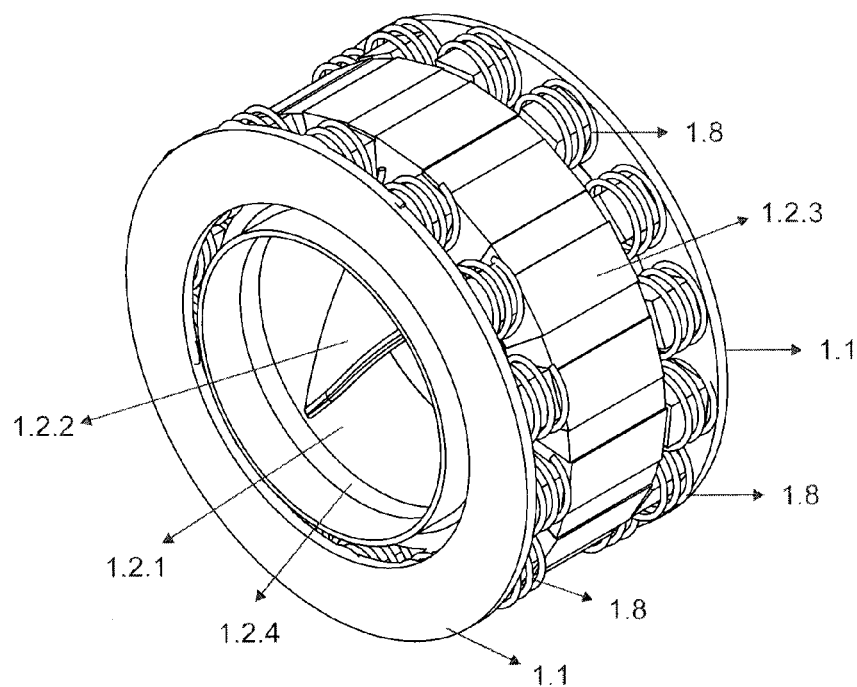

FIG. 5 The Exploded View Installed Without a Case

Figure 6:
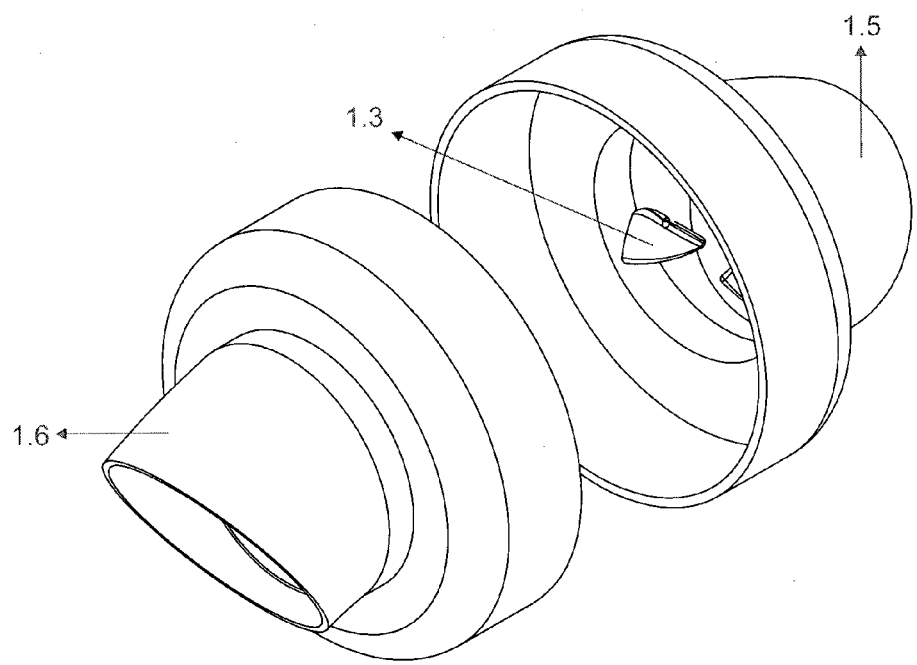

FIG. 6 The Exploded View with Exploded Case

Figure 7:
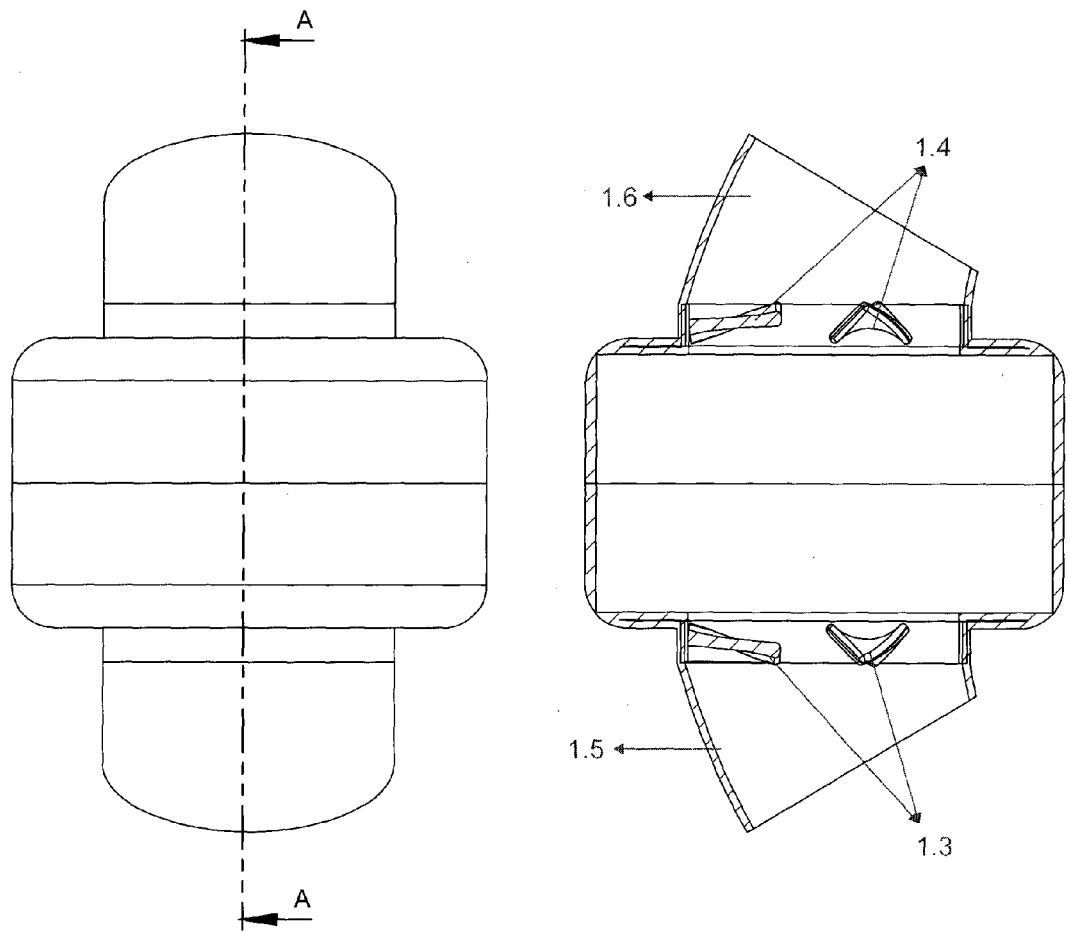

FIG. 7 The Cutaway View of the Case

Figure 8:
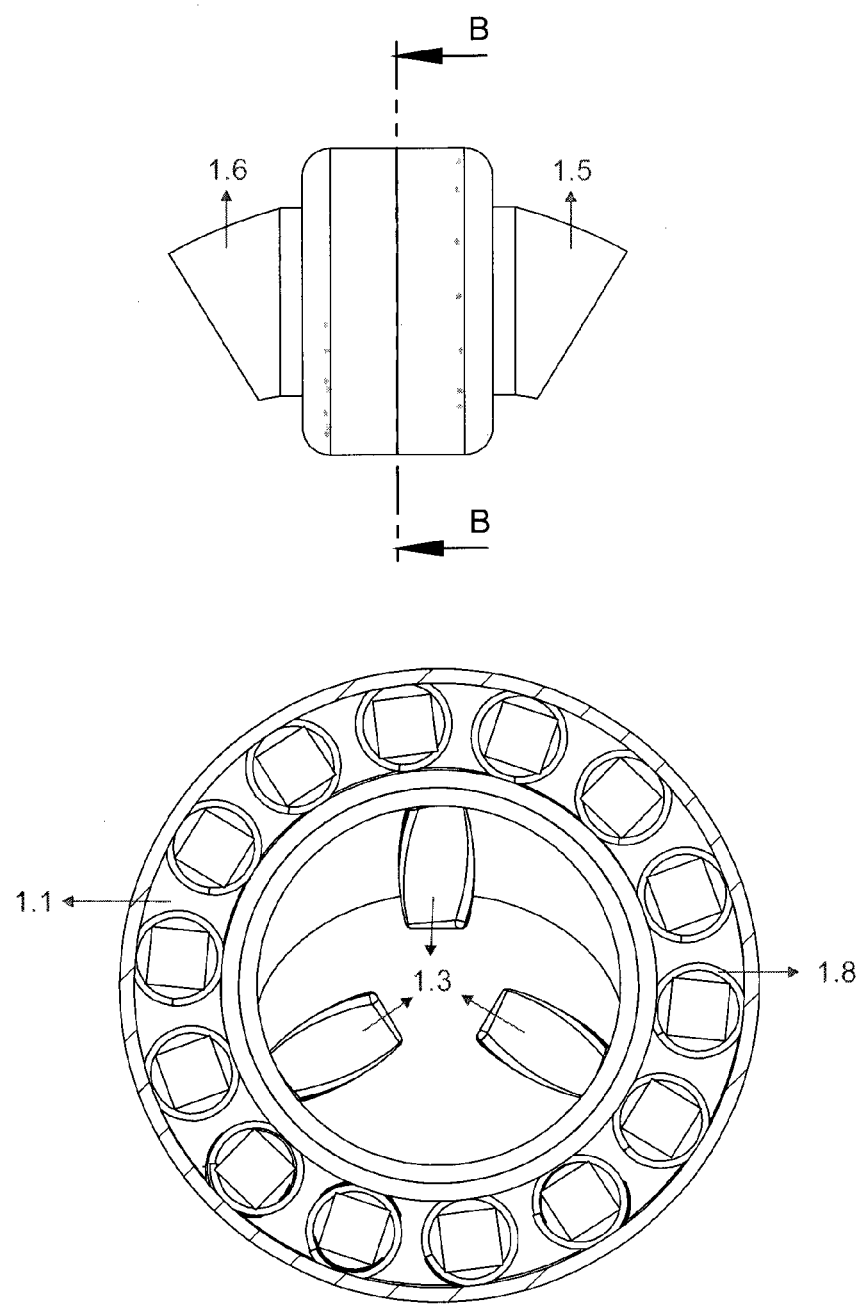
Figure 9:
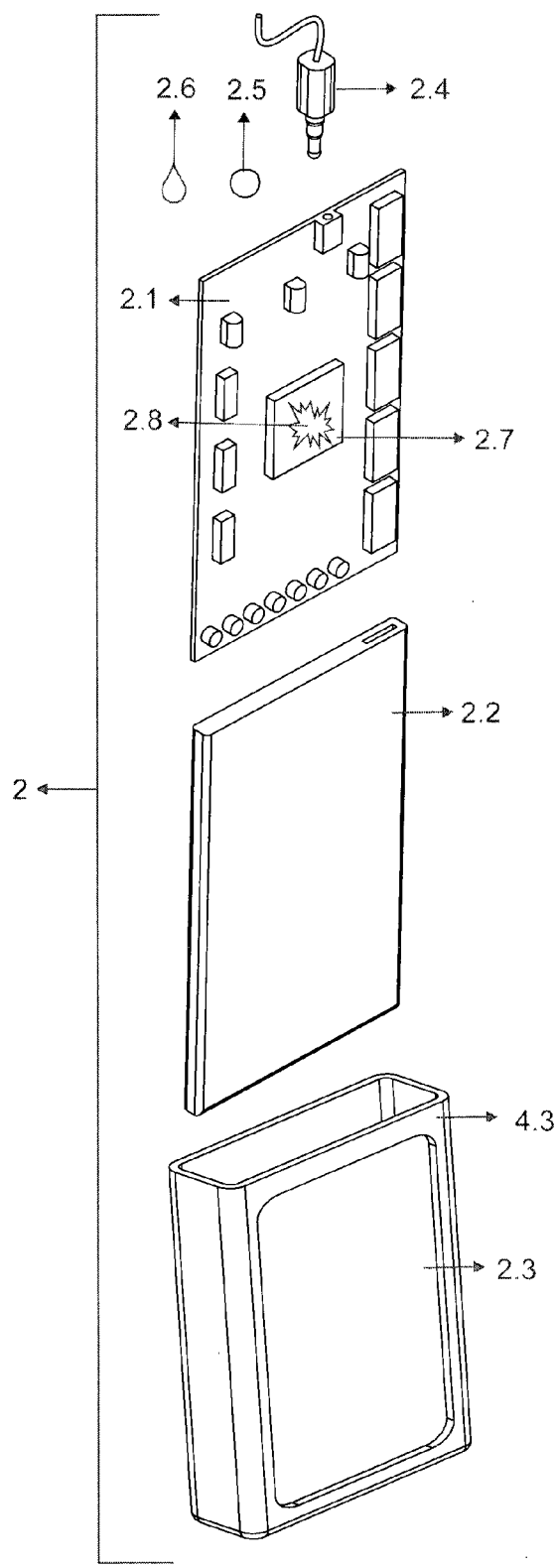
Figure 10:
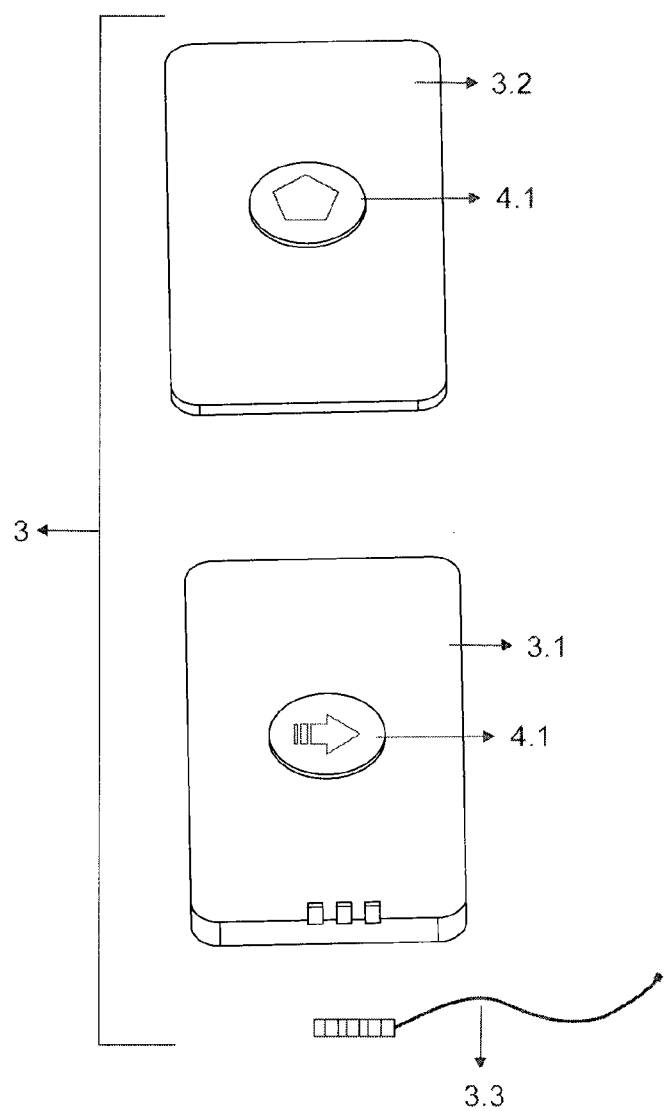
Figure 11:
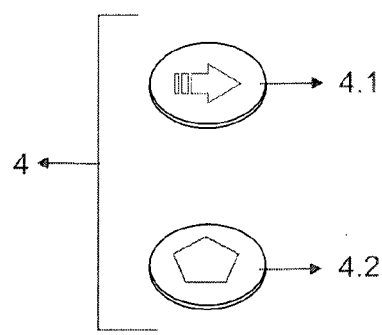

FIG. 8 The B-B Cutaway View of the Permanent Heart Assist Device with Double Stators FIG. 9 The General View of the Control Units FIG. 10 The General View of the Batteries FIG. 11 The General View of the Drivelines

DESCRIPTION OF THE REFERENCE NUMERALS

1. Motor
  1.1. Stator
  1.2. Rotor
    1.2.1. The Framework with Magnetic Property
    1.2.2. Helical Fan Blade
    1.2.3. Immobilized Magnet Bars
    1.2.4. Roller Bearing
  1.3. Blood Flow Smoother
  1.4. Blood Flow Regulating Diffuser
  1.5. Curved Inlet Part
  1.6. Curved Outlet Part
  1.7. Ceramic Roller
  1.8. Electric Coils 2. Control Unit
2.1. Internal Control Unit
2.2. External Control Unit
2.3. Touch Screen
2.4. ECG Wires
2.5. Pressure Sensor
2.6. Blood Flow Sensor
2.7. Microprocessor
2.8. Software
3. Batteries
3.1. Outer Battery
3.2. Inner Battery
3.3. Electric Power Cable
4. Wireless Power Transfer Apparatus
4.1. Outer wireless Energy Transfer Apparatus
4.2. Inner wireless Energy Transfer Apparatus
4.3. Protecting Cover

DETAILED DESCRIPTION OF THE INVENTION

The invention is composed of a motor (1); at least fixed two stators (1.1), a rotor (1.2), a blood flow smoother (1.3), a blood flow regulating diffuser (1.4), a curved inlet part (1.6), a curved outlet part (1.7) and electric coils (1.8). The rotor (1.2) includes; a framework made of material with magnetic property (1.2.1), helical fan blade (1.2.2), immobilized magnet bars (1.2.3) and a roller bearing (1.2.4). Control unit (2) comprises an internal control unit (2.1), an external control unit (2.2), a touch screen (2.3), ECG wires (2.4), a pressure sensor (2.6), a microprocessor (2.7) and software. Batteries (3) are made up of an inner battery (3.1), an outer battery (3.2) and an electric power cable (3.3), wireless energy transfer apparatus (4) contains an inner power transfer apparatus (4.1), an outer power transfer apparatus (4.2) and a protecting cover (4.3).

The brushless electric motor (1.), the main part of the heart assist device, is made up of at least two immobilized stators (1.1), and at least one mobile rotor (1.2). Stator (1.1) has at least two parts, and it is not located in the exterior of the rotor (1.2) but anterior and posterior of it. Rotor (1.2) can rotate freely inside the stator (1.1) on the rollers made of ceramic like durable materials.

The inside of the rotor (1.1), on which there are permanent magnet bars (1.2.3) with natural magnet properties, is hollow and as it has no pivot pin, the helical fan blade fixed inside the hollow rotor (1.2) integrate with the cylinder shaped rotor (1.2) and they push the blood from back to forward rotating together with the rotor (1.2). The poles of the permanent magnet bars (1.2.3) face both of the stators (1.1).

It is essential not to put pressure on the vital organs and blood vessels around both aorta and pulmonary artery. This new heart assist device we recommend is designed with motor (1) with double stators (1.1) so that its outer diameter can be smaller. Thus, stator (1.1) is located not in the outermost of the rotor (1.2) but anterior and posterior of it. Another advantage of the double stator (1.1) is that engine torque is enhanced nearly twice as much. When one of them fails for a variety of reasons, the stand-by stator starts running immediately, and this is a vital additional advantage.

Furthermore, there is a blood flow smoother (1.3) in the inlet of the device and a blood flow regulating diffuser (1.4) controlling the blood turbulence in the outlet of the device. Thanks to these two parts, the turbulence of the blood flowing into and out of the device is controlled completely. Moreover, as it has been designed to nm with more than one rotor (1.2), the turbulence of the blood is prevented by reversing one of the rotors.

Aorta and pulmonary artery do not pass straight but revolve in the thorax after commencing from the heart. Similarly, curved inlet part (1.5) and curved outlet part (1.6) have been designed compatible with these anatomic properties. This structure is not only a convenience for a surgeon to install the device but also it is a design appropriate for the natural blood flow.

This heart assist device is considerably smaller than the previous ones, so it can be applied trans aortic or trans pulmonary artery separately or together.

While it is installed trans aortic or trans pulmonary artery, additional artificial blood vessel or cannulae are not required as in the similar heart assist devices. This is an important and outstanding feature in two ways: Firstly, as in the DeBakey device, long artificial blood vessel and cannulae pose a grave resistance in front of the motor according to fluid mechanics. This increased resistance is accompanied by the excessive energy consumption.

Therefore, big batteries are required and consequently, battery lives are shortened. Since our device are installed into the aorta directly without any artificial blood vessels or cannulae, there will be no serious vessel resistance and the workload of the device will be less than its counterparts, and as a result, it will bring about small volume battery and long battery life. The second outstanding feature; as there are no artificial blood vessels or cannulae anterior or posterior of the device, it will reduce the blood contact with foreign surface. Thus, it will be a trouble-free device in terms of thromboembolic events when compared with its counterparts.

Heart assist device does not include a pivot pin. This property decreases its surface contact with blood and provides advantage against the complications that may occur in the shaped elements of blood and coagulation systems when compared with its counterparts.

Rotor (1.2) includes helical fan blade (1.2.2) positioned all around inside of it. Motor (1) runs with electric energy. When the motor (1) is supplied electricity, rotor (1.2) rotates with helical fan blade (1.2.2) inside it and provides a certain amount of flow to the blood passing through it with its pushing power.

Since the heart assist device is in a small volume, it can be applied to all patient bodies including little pediatric or newborn children.

Control units (2) regulates motor running. The system has two separate control units; one is internal control unit (2.1) the other is external control unit (2.2). Internal control unit (2.1) regulates motor (1) running, and also provides pulsatile blood flow like a healthy heart performing systole and diastole. Synchronized with the ECG signals, it turns the motor (1) in real-time. The diastole phase, when the whole heart is relaxed and the motor (1) stops, is a required and essential interval to provide coronary blood circulation. When the motor (1) stops at diastole phase, blood fills the coronary vessels by flowing backwards through the helical fan blade (1.2.2).

Heart assist device can be used by installing it into the aorta in the cases with left heart failure, and into the pulmonary artery in the cases with right heart failure. Heart assist device can be used by installing two separate motors (1) both trans aortic and trans pulmonary artery in the cases with left and right heart failure.

Another precaution to prevent the patient from feeling the vibrations of the heart assist device when it turns is that it is insulated with a biocompatible material like silicon which absorbs vibrations after the device is installed.

The device has two batteries, one inner (3.2) the other outer battery (3.1). The outer apparatus which includes the outer battery is hung on the shoulder or belt of the patient and can be charged with its adaptor. The outer apparatus can be used by positioning it directly at the wireless energy transfer point.

The outer apparatus include three separate equipments with three different functions. The first equipment is a chargeable lithium-ion battery (3.1) and it is a depot providing the required energy. The second equipment is the outer wireless energy transfer apparatus (4.1) which transfers power to the inner battery (3.2). The third is the external control unit (2.2). Thanks to its remote control property, the external control unit (2.2) displays the state of charge of the inner battery (3.2) and the vital data such as heart rate, blood pressure and blood flow in real-time on the touch screen (2.3) whenever they are demanded. Therefore, touch screen (2.3) of the external control unit (2.2) is on one side of the apparatus, and induction surface of the outer wireless energy transfer apparatus (4.1) which provides power transfer is on the other side of it.

The inner battery (3.2) and internal control unit (2.1) are placed together into a protecting cover (4.3). The cover can be made of any biocompatible material or nitinol. The adjustment of the internal control unit (2.1) can be changed from the touch screen (2.3) of the external control unit (2.2) after the authorized user's access.

The power from the outer battery (3.1) is transferred into the inner battery (3.2) through the help of the outer wireless energy transfer apparatus (4.1) and inner wireless energy transfer apparatus (4.2). There is a microprocessor (2.7) in the internal control unit (2.1), and its system adjustments can be changed from the touch screen (2.3) of the external control unit (2.2) after the authorized user's access.

The motor (1) mentioned above is a sort of brushless motor as can be seen. As you know, a drive line and a microprocessor (2.7) are required to run improved brushless motors. The microprocessor (2.7) in the internal control unit (2.1) performs this task. The microprocessor (2.7) can control the motor (1) comprehensively.

The ECG signals of the patient enter into the internal control unit. These signals are amplified by amplifier circuit and are read by the microprocessor through ADC (Analog to Digital Converter). Microprocessor starts or stops motor in turn at the time of systole and diastole analyzing these signals.

The surface of the motor (1) that will contact with blood and tissues will be coated with a special insulation material like nickel-titanium alloy in order to prevent various harmful ions to enter blood and expose the system to corrosion, the electric equipment of the system will be insulated from blood with one of the dielectric biocompatible materials.

Rotor (1.2) is hollow and contains at least two helical fan blade (1.2.2) on its ironwork. As the points of attachment where fan blade are attached to the rotor are elastic and foldable, fan blade open while rotor rotates rapidly and provide driving power and when rotor stops, they become parallel with the interior surface and empty vessel lumen. Thus fan blade will not hinder blood flow in the aorta if the heart failure improves after some time or rotor fails for technical reasons. If the heart failure does not get better, then the heart assist device has been designed as an permanent device to last for a life time installed to the patient and to continue running and assisting heart until the patient dies.

The speed of the rotor turning speed will be adjusted in real-time by the microprocessor (2.7) according to the ECG signals received and it will increase and decrease synchronously. When the ECG signals are not received, the speed of the rotor will be determined and applied by the microprocessor (2.7) automatically with the rotating speed previously established and set according to the condition of the patient by his/her doctor.

Blood pressure will be followed nonstop with the blood pressure sensors (2.5), and the most optimal rotor speed will be determined by processing the obtained data with the software (2.8). There will be an adjustment menu with the upper and lower limits of the rotor speeds determined previously.

Blood pressure sensors (2.5) and blood flow sensors (2.6) will be placed into the aorta with the device and by processing blood pressure values in the software in real-time, the rotor speed will be accelerated or decelerated by the microprocessor (2.7).

Heart surgeon installs the system with a suitable incision on the aorta and then the incision is repaired with an appropriate technique and the thoroughness of the vessel is not lost. This heart assist device will enable pulsatile blood flow for the patient by starting and stopping in turn or slowing down synchronous with the signals received from the ECG signals of the patient. As is known, a healthy individual has a pulsatile blood flow, pulsatile blood flow has more advantages in tissue perfusion when compared with continuous flow.

Natural anatomic structure of the aorta and pulmonary artery is curved, and blood naturally flows in this curved line. This heart assist device is also designed as curved compatible with the natural structure of the vessels. Motor contains a curved inlet part (1.5) and a curved outlet part (1.6) in the outlet of it. The fact that these parts can be assembled or disassembled on the motor easily, the required torsion angle between themselves can be set by turning them, it has a articulation that enables to adjust torsion angle most compatible with the anatomic structure of the aorta and pulmonary artery will make a great contribution to heart surgeons.

There are at least two or more fan blade inside the curved inlet part (1.5) and a curved outlet part (1.6) and they integrate with them. The task of these fan blade is that they provide smooth blood flow into the device and prevent turbulence out of the outlet. The fan blade in the inlet part are called blood flow smoothers (1.3), and the fan blade in the outlet part are called blood flow regulating diffuser (1.4), and these fan blade have designed specially. These fan blade integrate with the pivot pin in DeBakey's and other devices, and this leads to a grave hemodynamic resistance in front of the motor. Therefore, our device brings advantage as it has no pivot pin.

The rotor (1.2), rotates on the ceramic roller (1.7) rotating on the roller bearing (1.2.4) made of ceramic like material that is not eroded away by friction and biocompatible. Therefore, it is anticipated that motor will function properly for many years without abrasion.

Motor (1.1) is brushless, with single phase or three-phase, synchronous servo motor and runs with undervoltage direct current or alternating current that does not harm human. Stator (1.1) is made up of at least two parts. Rotor (1.2) turns between two stators (1.1). Stator is made from overlapped silicic sheet metals, and electric coils (1.8) made of wires with high electrical conductivity are placed into the cavity on it. The connection of the coils of the stator (1.1) are designed so that both stators (1.1) turn the rotor in the same direction, so it turns more powerfully and its torque is doubled.

The inside of the rotor (1.2) is hollow and contains helical fan blade (1.2.2). The number of the helical fan blade (1.2.2) can be two or more. As they were located in the angles of blood flow direction, the helical fan blade (1.2.2) that rotate with rotor (1.2) push blood from back to forward and provide enough blood flow to the patient.

There are small fan blade in the inlet of the device called blood flow smoother (1.5) and in the outlet of the device called blood flow regulating diffuser (1.4). As it has no pivot pin, these fan blade are placed inside the curved inlet part (1.5) in the inlet side and curved outlet part (1.6) in the outlet side so that they can integrate with them. Thus, blood flow is smoothed in the entry and likely turbulence in the exit is prevented.

Helical fan blade (1.2.2) should not cause a serious resistance or obstruction in front of the heart when rotor (1.2) fails due to a technical reason. Therefore, the number of fan blade, their surface width and fan blade angles have been designed so that they have a reasonable resistance.

The curved inlet part (1.5) and curved outlet part (1.6) can be assembled or disassembled on the motor easily, the required torsion angle between themselves can be set by turning them, and torsion angle can be adjusted most compatible with the anatomic structure of the aorta and pulmonary artery of the patient.

After the signal received from the ECG connection (2.4) are processed in real time, motor starts and stops in turn ECG rhythm, and thus, pulsatile blood flow is achieved. Furthermore, it is accelerated when the heart rate of the patient increases or it is decelerated when the heart rate of the patient decreases.

Pressure sensors (2.5) and blood flow sensors (2.6) measure blood pressure and blood flow in the aorta in real time and send messages to microprocessor (2.7) in real time.

Microprocessor (2.7) receives the signals from ECG connection (2.4), pressure sensors (2.5) and blood flow sensors (2.6) synchronously and processes and uses algorithm matching with its own private software (2.8).

Motor drive circuit, inner battery charge circuit and data transfer circuit are located together in a protecting cover (4.3).

External control unit (2.2) has a touch screen (2.3) and includes wireless energy transfer apparatus, outer battery (3.1), data transfer circuits and electric power cable (3.3) input.

Batteries (3) consist of two separate batteries, outer battery (3.1) and inner battery (3.2). Power from the other battery to the inner battery is transferred via outer wireless energy transfer apparatus (4.1) and inner wireless energy transfer apparatus (4.2) of the wireless energy transfer apparatus (4).

The inlet and outlet parts of the device is designed so that they can be assembled and disassembled to the motor easily in case it may require to replace the heart assist device due to technical problems. Thus only the motor can be changed by a heart surgeon (1).

The corners are designed with radius edges so that blood coagulation can not occur on the corner surfaces where blood contacts.

The invention claimed is:

1. A heart assist device installed as trans arterial, patients with end-stage heart failure, comprising:
   a motor which includes a plurality of fixed stators;
   a ceramic roller;
   a rotor rotating freely on the roller;
   a plurality of blood flow smoothers in a curved inlet part;
   and a curved outlet part with a plurality of blood flow regulating diffusers.

2. The heart assist device of claim 1, wherein the rotor contains a roller bearing where the ceramic roller is located.

3. The heart assist device of claim 1, wherein the stator is made from two parts installed acing one another in the anterior and posterior of the rotor.

4. The heart assist device of claim 1, wherein the rotor contains a plurality of permanent magnet bars installed with poles of the bars facing both of the stators.

5. The heart assist device of claim 1, wherein the rotor contains a plurality of helical fan blades with enough surface width and fan blade angles do not cause an obstruction or a resistance in front of a blood flow when the rotor fails due to any technical problems.

6. The heart assist device of claim 1, wherein the curved inlet part and the curved outlet part are compatible with a natural anatomic structure of a curved aorta and a pulmonary artery, which enable blood to pass without being hindered from its natural flow.

7. The heart assist device of claim 1, wherein the curved inlet part and the curved outlet part have articulated structures which enable to set a required torsion angle between the curved inlet part and the curved outlet part by turning the curved inlet part and the curved outlet part and to adjust the torsion angle most compatible with the anatomic structure of a patient.

8. The heart assist device of claim 1, wherein the plurality of blood flow smoothers are configured to regulate blood flow entering the motor.

9. The heart assist device of claim 1, wherein the plurality of blood flow regulating diffusers are configured to regulate to prevent a blood turbulence in the outlet of the motor.

10. The heart assist device of claim 1, wherein the plurality of blood flow smoothers and the plurality of blood flow regulating diffusers have high heat conductivity and are made of biocompatible materials.

11. The heart assist device of claim 1, wherein all surfaces of the motor contacting with body are coated with a biocompatible material that provides heat insulation.

12. The heart assist device of claim 1, wherein the motor is coated with a biocompatible material which absorbs vibrations that occurs when motor starts and stops.

13. The heart assist device of claim 1, wherein the rotor comprises at least two helical fan blades, the at least two helical fan blades are elastic and foldable.

14. The heart assist device of claim 13, wherein the helical fan blades open while rotor rotates, the helical fan blades become parallel with the interior surface and empty vessel lumen when rotor stops.

15. The heart assist device of claim 1, wherein the plurality of blood flow smoothers are a plurality of fan blades integrated with the curved inlet part without pivot pins.

16. The heart assist device of claim 1, wherein the plurality of blood flow regulating diffusers are a plurality of fan blades integrated with the curved outlet part without pivot pins.

* * * * *